US009107628B2

(12) United States Patent
Huels et al.

(10) Patent No.: US 9,107,628 B2
(45) Date of Patent: Aug. 18, 2015

(54) VIDEO LARYNGOSCOPE WITH DISPOSABLE BLADE

(71) Applicants: Dieter Huels, Stockach (DE); Eugenia Fuhr, Tuttlingen (DE); Ulrich Merz, Villingen-Schwenningen (DE); Martin Renner, Liptingen (DE); Fabian Zimmerli, Warth (CH)

(72) Inventors: Dieter Huels, Stockach (DE); Eugenia Fuhr, Tuttlingen (DE); Ulrich Merz, Villingen-Schwenningen (DE); Martin Renner, Liptingen (DE); Fabian Zimmerli, Warth (CH)

(73) Assignee: KARL STORZ GMBH & CO. KG (DE)

( * ) Notice: Subject to any disclaimer, the term of this patent is extended or adjusted under 35 U.S.C. 154(b) by 281 days.

(21) Appl. No.: 13/651,150

(22) Filed: Oct. 12, 2012

(65) Prior Publication Data
US 2014/0107422 A1    Apr. 17, 2014

(51) Int. Cl.
| | | |
|---|---|---|
| *A61B 1/267* | (2006.01) | |
| *A61B 1/05* | (2006.01) | |
| *A61B 1/06* | (2006.01) | |
| *A61B 1/00* | (2006.01) | |

(52) U.S. Cl.
CPC .............. *A61B 1/267* (2013.01); *A61B 1/00105* (2013.01); *A61B 1/00142* (2013.01); *A61B 1/05* (2013.01); *A61B 1/0676* (2013.01); *A61B 1/0684* (2013.01)

(58) Field of Classification Search
CPC ....... A61B 1/00105; A61B 1/05; A61B 1/267
USPC .......... 600/185, 188, 190, 193–194, 197–199
See application file for complete search history.

(56) References Cited

U.S. PATENT DOCUMENTS

| | | | |
|---|---|---|---|
| 4,592,343 A | | 6/1986 | Upsher |
| 5,135,489 A | * | 8/1992 | Jepson et al. .................... 604/48 |
| 5,261,392 A | * | 11/1993 | Wu ................................ 600/188 |
| 5,287,848 A | | 2/1994 | Cubb et al. |
| 5,363,838 A | | 11/1994 | George |
| 5,381,787 A | | 1/1995 | Bullard |
| 5,645,519 A | | 7/1997 | Lee et al. |
| 5,800,344 A | | 9/1998 | Wood, Sr. et al. |
| 5,827,178 A | | 10/1998 | Berall |
| 6,543,447 B2 | | 4/2003 | Pacey |
| 6,655,377 B2 | | 12/2003 | Pacey |
| 6,719,688 B2 | * | 4/2004 | Pecherer et al. ............... 600/199 |
| 7,946,981 B1 | * | 5/2011 | Cubb ............................ 600/194 |
| 8,414,481 B2 | * | 4/2013 | Hakanen et al. ............... 600/196 |
| 8,747,389 B2 | * | 6/2014 | Goldfarb et al. ........... 604/891.1 |

(Continued)

FOREIGN PATENT DOCUMENTS

| | | |
|---|---|---|
| EP | 1307131 B1 | 5/2003 |
| JP | H05292504 A | 11/1993 |
| WO | 9715144 A1 | 4/1997 |

OTHER PUBLICATIONS

A.P. Advance Brochure; 2011; 4 pages.

(Continued)

*Primary Examiner* — Larry E Waggle, Jr.
(74) *Attorney, Agent, or Firm* — Whitmyer IP Group LLC

(57) ABSTRACT

An intubation instrument for intubating a patient's trachea including an imager module having a base unit with a finger loop and a longitudinal member attached to the distal end of the base unit, as well as a blade having a handle that is hollow and mates with the outer surface of the longitudinal member forming a male-female connection, the distal end of the blade projecting laterally therefrom, the distal end of the blade being insertable into a human during intubation.

22 Claims, 9 Drawing Sheets

(56) References Cited

U.S. PATENT DOCUMENTS 8,834,360 B2 * 9/2014 Plevnik et al. ............... 600/188
2010/0249513 A1 * 9/2010 Tydlaska ...................... 600/186

OTHER PUBLICATIONS

Airtraq Guided Intubation Brochure—Feb. 14, 2012; 4 pages.
GlideScope Cobalt AVL Verathon Medical Brochure; 2009; 2 pages.
GlideScope GVL® and Cobalt User's Manual & Quick Reference Guide; 0900-1204-07-20; Jan. 11, 2012; 91 pages.
McGrath® Video Laryngoscope | Series 5 Brochure—Undated; 2 pages, Copyright 2011.
McGrath® MAC; Copyright 2011 Aircraft Medical Limited; 4 pages.
Aircraft Medical; McGrath—The World's First Fully Portable Video Laryngoscope; Copyright 2004 Aircraft Medical LTD; 2 pages.
Pentax Brochure; Sep. 12, 2007; 2 pages.
Crosby, Techniques using the Bullard Laryngoscope, Anesthesia and Analgesia 81: 1314-1315 (1995).

* cited by examiner

VIDEO LARYNGOSCOPE WITH DISPOSABLE BLADE

FIELD OF THE INVENTION

This invention is directed to an intubation system and tools for intubation. The invention is particularly useful in various procedures for intubating a patient's trachea.

BACKGROUND OF THE INVENTION

Intubation instruments such as video laryngoscopes are known in the art. Known laryngoscope systems include U.S. Pat. No. 5,827,178 to Berall; U.S. Pat. No. 6,665,377 to Pacey; U.S. Pat. No. 6,543,447 to Pacey; U.S. Pat. No. 5,287,488 Cubb et al.; Japanese Patent No. JPH05-292504; U.S. Pat. No. 5,645,519 to Lee; U.S. Pat. No. 5,800,344 to Wood; U.S. Pat. No. 5,363,838 to George; U.S. Pat. No. 5,381,787 to Bullard; Crosby, Techniques using the Bullard Laryngoscope, Anesthesia and Analgesia 81: 1314-1315 (1995); WO 97/15144 to Shapiro; and U.S. Pat. No. 4,592,343 to Upsher.

Known commercial laryngoscope systems include the Pentax AIRWAY SCOPE and the Verathon GLIDESCOPE RANGER. However, these laryngoscope systems suffer from various deficiencies.

One problem known to laryngoscopes is that the imager shaft may become twisted when being inserted into a blade element. If the imager shaft is not inserted correctly into the blade element, then the imager shaft may become stuck and the image produced by the camera does not appear upright or appears off-center in a display.

Other problems known in the prior art involve the cable becoming damaged when the imager shaft is pulled out of the single-use blade after use. Another known problem in the prior art involves difficulties in disinfecting the imagers in known laryngoscope systems.

Thus, it is desirable to provide a video laryngoscope system that overcomes and solves these above mentioned problems.

SUMMARY OF THE INVENTION

Accordingly, it is an object of the invention to provide a laryngoscope system that overcomes and solves the above mentioned problems in the prior art. It is an object of the invention to provide a video laryngoscope with disposable blade, such that the blade is a single-use blade.

It is another object of the invention to provide a video laryngoscope where the imager shaft does not become stuck when the imager shaft is inserted into the blade.

These objects of the invention are achieved by providing an intubation instrument comprising: an imager module, the imager module including a base unit having a proximal end and a distal end, the proximal end of the base unit having a finger loop, and a longitudinal member, the longitudinal member attached to the distal end of the base unit and projecting longitudinally away from the distal end of the base unit; and a blade, the blade having a proximal end and a distal end, the proximal end forming a handle that is hollow and that mates with the outer surface of the longitudinal member forming a male-female connection, and the distal end of the blade projecting laterally therefrom, the distal end of the blade being insertable into a human during intubation.

In certain embodiments, the base unit includes a flange at the distal end of the base unit, the flange on the base unit abutting against a flange in the proximal end of the blade. This flange to flange abutment is beneficial as it prevents moisture or fluids from entering into the hollow portion of the handle, thus, insulating the imager module from moisture and/or fluids.

In certain embodiments, the longitudinal member includes a ball plunger on the outside surface of the longitudinal member. The ball plunger may be flexible and may have a spring between it and the outer surface of the longitudinal shaft, such that when force is exerted on the ball plunger, it retracts into the longitudinal member, however, it is forced outward by the spring, when no external force is provided on the ball plunger.

In certain embodiments, the blade includes a ball detent on the inside surface of the handle of the blade, the ball detent adapted to interact with the ball plunger of the longitudinal member so that the longitudinal member and blade are connected with each other during use of the intubation instrument.

In certain embodiments, when in use, the ball plunger of the longitudinal member locks into the ball detent on the inside surface of the handle of the blade to lock the blade to the longitudinal member.

In certain embodiments, the intubation instrument further comprises electronic wiring, the electronic wiring containing a camera at its distal end.

In certain embodiments, the imager module and the blade are adapted to receive the electronic wiring, the electronic wiring passing through the imager module and the blade.

In certain embodiments, the blade includes a guide located within the handle of the blade, the guide including a channel.

In certain embodiments, the channel is adapted to receive electronic wiring, the electronic wiring containing a camera at its distal end.

In certain embodiments, the electronic wiring is connected to a display for displaying images received by the camera.

In certain embodiments, the electronic wiring is partially contained in the distal end of the blade.

In certain embodiments, the longitudinal member includes electronics to control the imager module. The electronics may include electronics for the camera located at the distal end of the cable.

In certain embodiments, the base unit includes a hollow portion having a loop, the hollow portion adapted to receive electronic wiring.

In certain embodiments, the blade is disposable. In certain embodiments, the blade is made of plastic or a hard polymer material.

In certain embodiments, the intubation instrument is a video laryngoscope.

In certain embodiments, the imager module is separable from the blade, wherein the imager module is disinfected after being used and the blade is disposed of after use.

In certain embodiments, the electronic wiring is flexible. In certain embodiments, the electronic wiring does not kink.

In certain embodiments, the blade includes a lens at its distal end. In certain embodiments, the lens has a rectangular shape. In certain embodiments, the lens is a single, a doublet or may include more than one lens.

In certain embodiments, the electronic wiring passes through a loop portion in the base unit.

In certain embodiments, the channel in the blade is sandblasted for easier insertion and removal of the electronic wiring.

In certain embodiments, the imager module is disinfected after use and then is used again, while the blade is disposed of and is a single-use blade. In certain embodiments, the handle is part of the single-use blade.

Other objects of the invention are achieved by providing an intubation instrument comprising: an imager module, the imager module including a base unit having a proximal end and a distal end, the proximal end of the base unit having a finger loop, and a longitudinal member, the longitudinal member attached to the distal end of the base unit and projecting longitudinally away from the distal end of the base unit, the longitudinal member having a ball plunger on the outside surface of the longitudinal member; and a blade, the blade having a proximal end and a distal end, the proximal end forming a handle that is hollow and that mates with the outer surface of the longitudinal member forming a male-female connection, and the distal end of the blade projecting laterally therefrom, the distal end of the blade being insertable into a human during intubation, the blade including a ball detent on the inside surface of the handle of the blade, the ball detent adapted to interact with the ball plunger of the longitudinal member so that the longitudinal member and blade are connected with each other during use of the intubation instrument, wherein when in use, the ball plunger of the longitudinal member locks into the ball detent on the inside surface of the handle of the blade to lock the handle to the longitudinal member and handle.

In certain embodiments, the blade is disposable blade. In certain embodiments, the intubation instrument is a laryngoscope.

In certain embodiments, the intubation instrument further comprises electronic wiring. In certain embodiments, the electronic wiring is located within the proximal end of the imager module. In certain embodiments the shape of the proximal end of the imager module matches the opening in the single-use blade so that incorrect insertion of the imager module into the blade is prevented.

In certain embodiments, the intubation instrument further comprises a guide inside the handle of the blade. In certain embodiments, the guide includes a channel. In certain embodiments, the channel is adapted to receive electronic wiring containing a camera at its distal end. In certain embodiments, the guide interacts with ball plunger on imager module, so imager module is inserted properly into the blade.

In certain embodiments, the channel in the blade is sandblasted for easier insertion/removal of the imager module, as less friction in the inside of the handle is created. In certain embodiments, the handle is sandblasted on the outside for a better grip.

In certain embodiments, the finger loop portion makes it easy for a user to manipulate the imager module. The finger loop makes it easier to remove the longitudinal member and prevents kinking of the cable during use. Moreover, the finger loop helps lead the cable away from the instrument and from the patient so it is not in the way during intubation.

This finger loop is advantageous as it solves kink problems of the cable and assists in removal of the blade from the imager module, which is advantageous as prior art systems become stuck together after use as moisture can cause these elements to become stuck to one another. The present invention includes the finger loop design, whereby easy separation of the blade and imager module is possible.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

Figure 1:
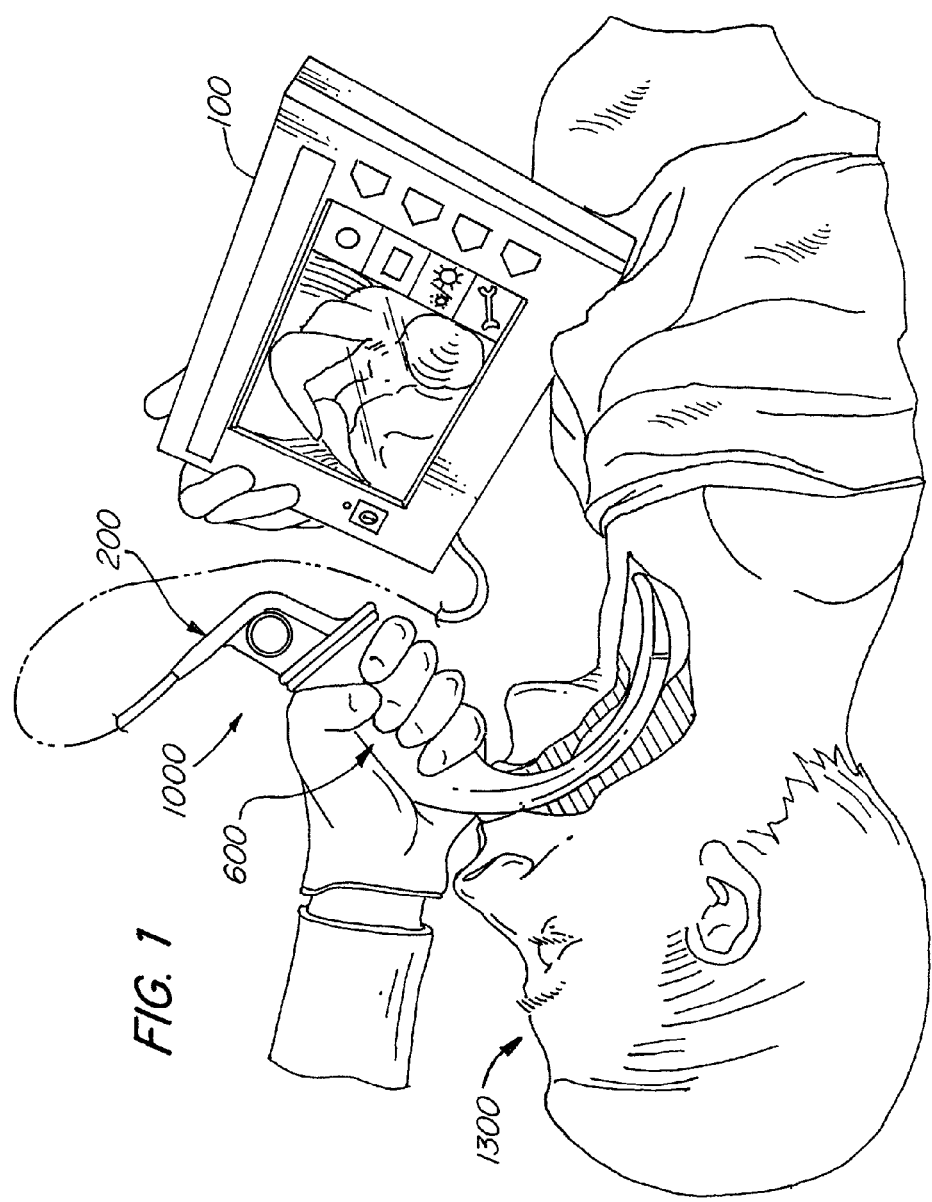
FIG. 1 is a perspective view of the video laryngoscope used in a patient.

Referring to FIG. 1 a perspective view of intubation instrument 1000 is shown being used in a patient 1300. The intubation instrument 1000 is shown entering the patient 1300 through the patient's mouth. The intubation instrument 1000 extends just outside a patient's trachea, thus, providing views of a patient's trachea.

The intubation instrument includes blade 600 attached to imager module 200. The imager module 200 has a cable or electronic wiring that is connected to display 100. The display 100 may be a video monitor, computer, or other screen where an image produced from the imager module 200 may be displayed, so that a doctor or nurse may view into the patient. In certain embodiments, the display can be directly attached to the handle of the laryngoscope or to the imager module 200.

Figure 2:
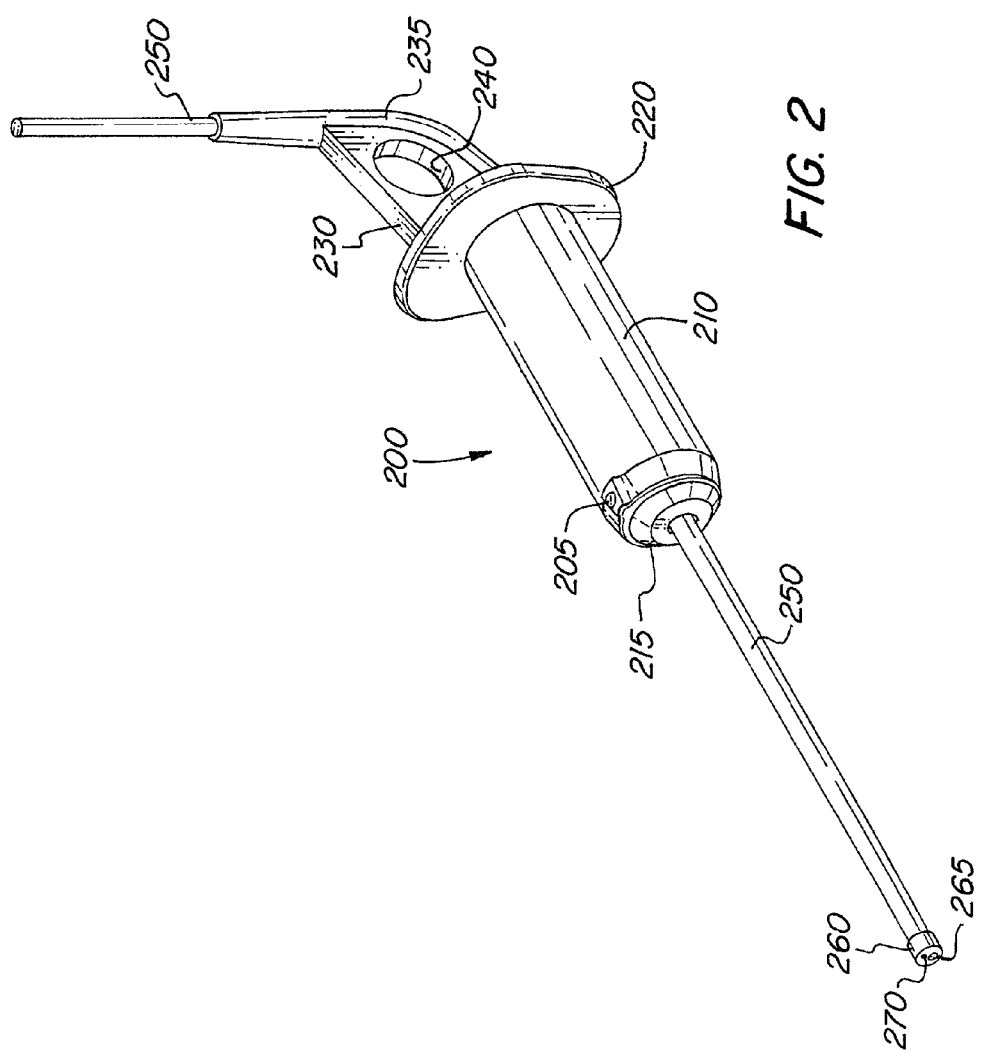
FIG. 2 is a perspective view of the imager module of FIG. 1.

FIG. 2 shows a perspective view of the imager module 200 of FIG. 1. Imager module 200 includes a base unit 230 and a longitudinal member 210 (also considered to be a longitudinal shaft).

The base unit as shown includes finger loop 240, flange 220, and cable 250. The cable 250 may also be referred to as electronic or electrical wiring. The finger loop may allow a surgeon or doctor to manipulate the imager module 200.

The longitudinal member 210 is shown having a ball plunger 205 on the outside surface of the longitudinal member 210. The longitudinal member 210 also has a front surface 215. The front surface 215 is fitted to abut an inner surface of the handle 610 (shown in FIG. 11).

Cable or electrical wiring 250 is shown passing through the imager module 200 including the base unit 230 and longitudinal member 210. The cable 250 passes by the finger loop 240 and through the longitudinal member 210. The cable 250 is flexible and has an imaging unit 260 at its distal tip. The imaging unit includes a light source 270 (such as an LED) and a camera unit 265 that is able to take an image during use. The camera unit 265 can be a CMOS sensor or any other solid-state image sensor. In certain embodiments, the distal part of imaging unit 260 can be a black plastic part that reduces reflections and scattered light from an LED. This solves a problem because the LED is inside the blade and light can be scattered by the inside walls of the blade or the distal window or lens. In certain embodiments, the black plastic part may be made of PEEK.

Figure 3:
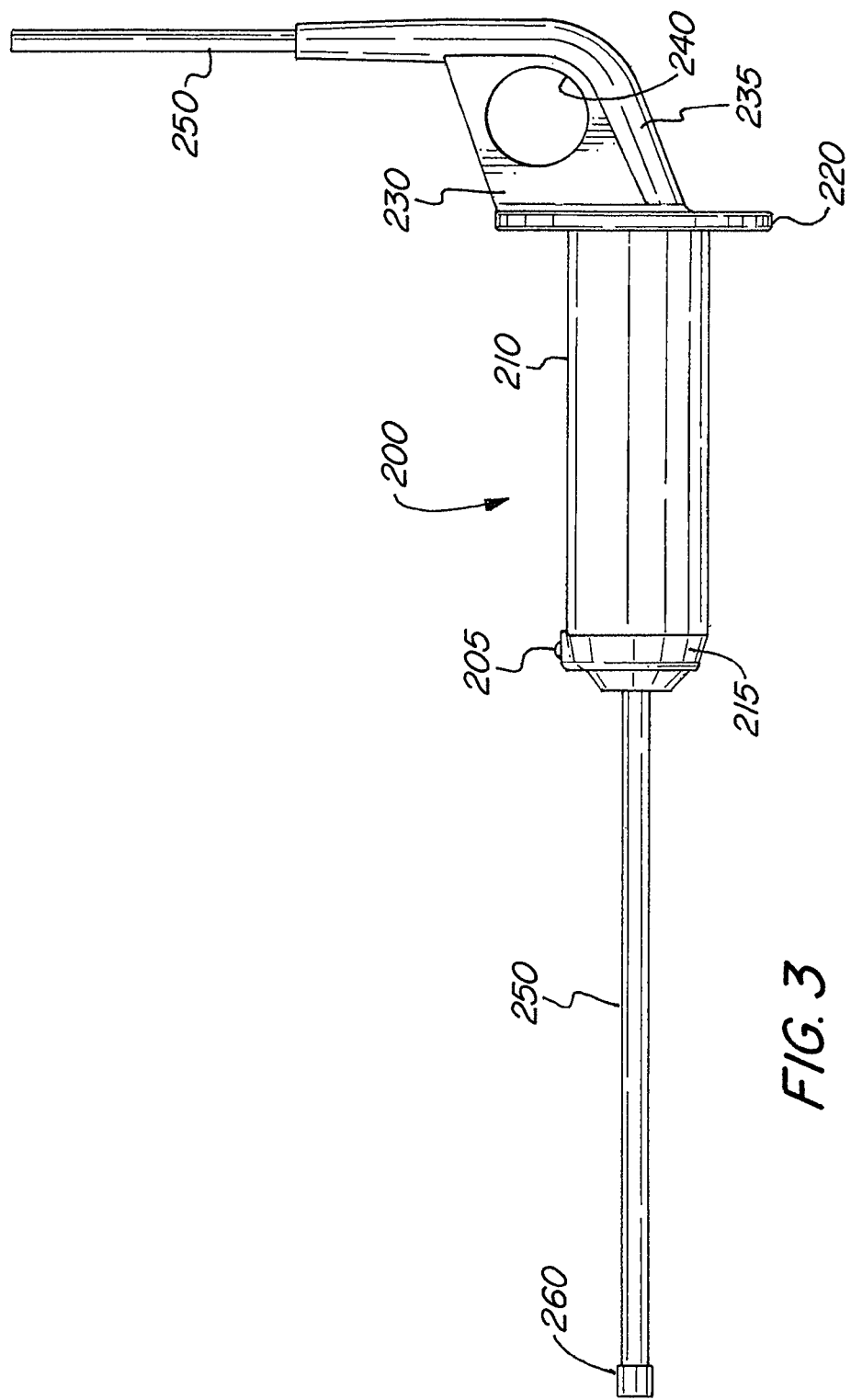
FIG. 3 is a side view of the imager module of FIG. 1.
Figure 4:
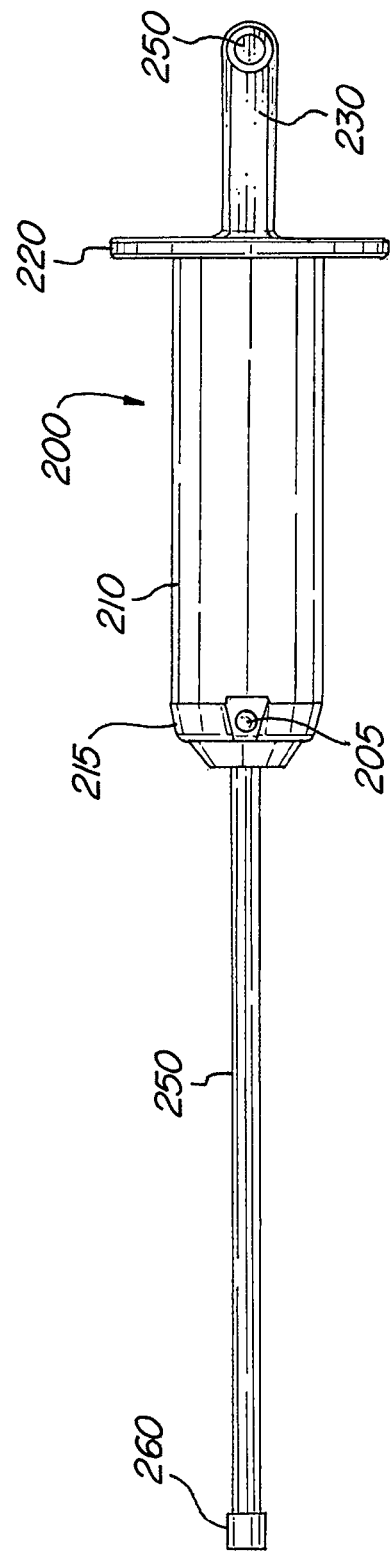
FIG. 4 is a top view of the imager module of FIG. 1.
Figure 5:
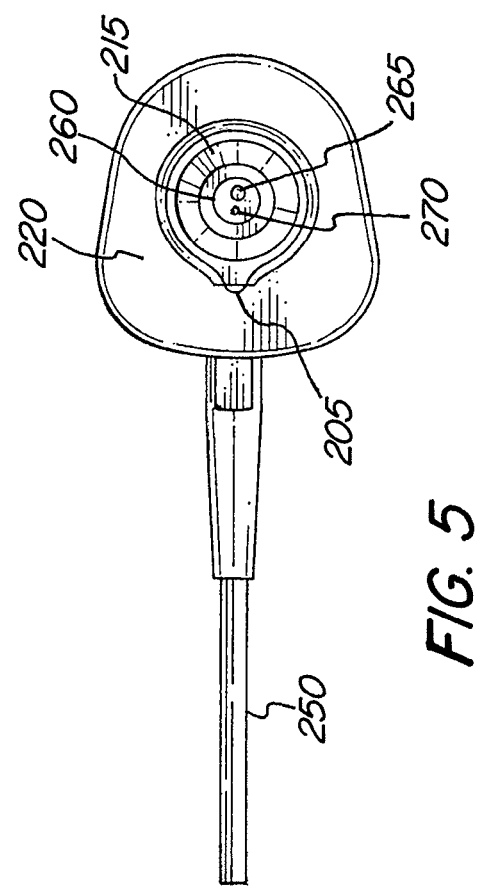
FIG. 5 is a front view of the imager module of FIG. 1.

FIGS. 3-5 show various views of imager module 200. These figures show a side, top, and front view of the imager module 200. It is shown in FIG. 3 that the flange 220 is perpendicular to the longitudinal member 210.

It is also shown in FIG. 3 that the cable 250 is flexible as it is able to be rotated 90 degrees through the base unit 230 and into the longitudinal member 210.

Figure 6:
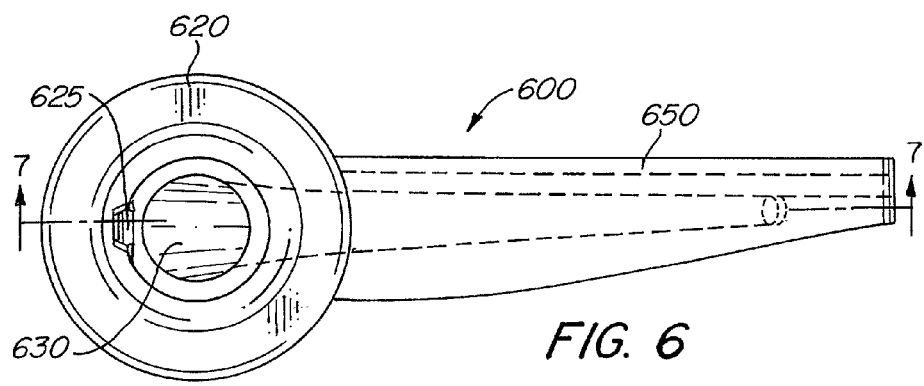
FIG. 6 is a top view of the blade of FIG. 1.

FIG. 6 is a top view of the blade 600 shown in FIG. 1. Blade 600 includes a guide 625 on the inside surface of the handle 610 of the blade 600. The blade 600 is also shown having a handle 610 having a channel 630 for reception of the longitudinal member 210. In broken lines, the distal part 650 of the blade is shown. It is this distal part 650 of the blade that extends just outside a patient's trachea.

Figure 7:
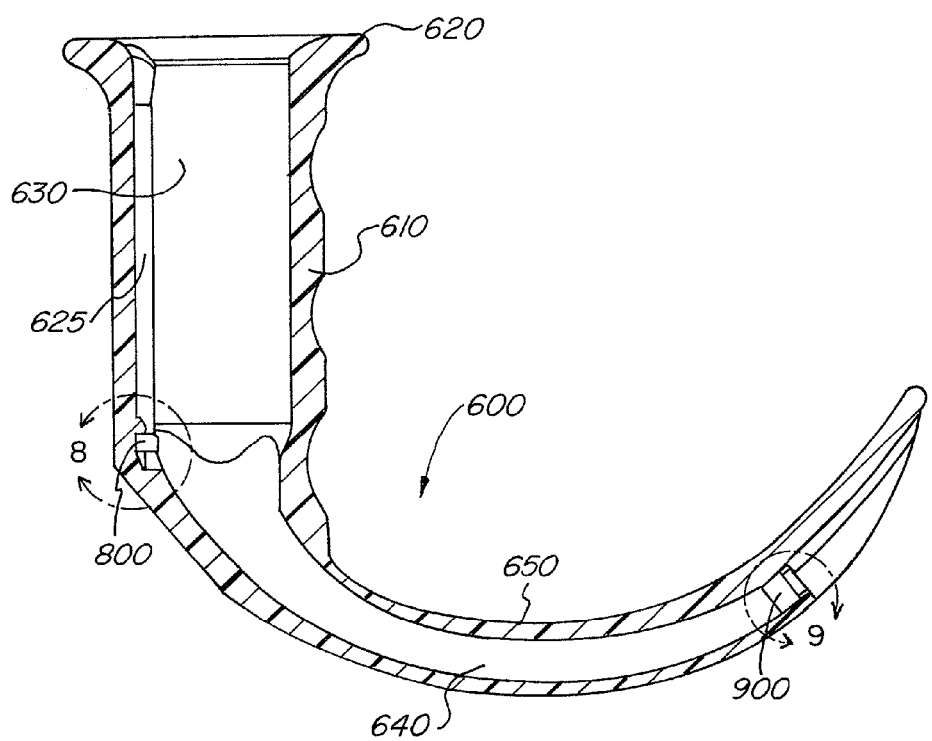
FIG. 7 is a cross section view of the blade of FIG. 6.

In FIG. 7, a cross section view of the blade of FIG. 6 is shown along axis 7-7. Here, the blade 600 is shown having a handle section 620 at the proximal end of the blade 600 with distal part 650 extending substantially perpendicular to the handle 610.

The handle 610 is shown having a hollow middle portion 630, the hollow portion 630 adapted to receive the imager module 210. The handle 610 includes a guide portion 625, the guide portion 625 used for guiding the imager module 210, so that it is placed into the proper position so ball plunger 205 is aligned with the ball detent. The handle 610 has section 800, shown in more detail in FIG. 8.

The distal part 650 of blade 600 has a channel 640. The distal part 650 is curved for easy access into the throat of a patient and just outside a patient's trachea. Furthermore, distal part 650 is shown having section 900, shown in more detail in FIG. 9.

Figure 8:
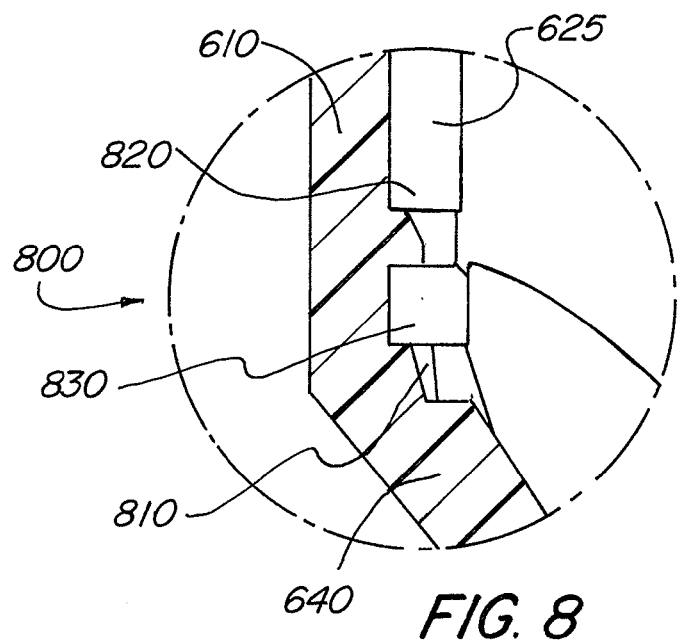
FIG. 8 is an exploded detail view along axis 8 of FIG. 7.

FIG. 8 is an exploded detail view of section 800 of FIG. 7. This is also shown along axis 8 in FIG. 7. FIG. 8 shows guide 625 for guiding the imager module into the hollow part 630 of the handle 610. Here, ball detent 830 is shown adapted to interact with the ball plunger 205 of the longitudinal member 210 so that the longitudinal member 210 and blade 600 are connected with each other during use of the intubation instrument 1000.

FIG. 8 also shows ridge 820, where the ball plunger 205 passes over the ridge and settles into ball detent 830. Furthermore, tapered surface 810 is also shown whereby upon applying pressure downwards, the ball plunger 205 is able to slide down the tapered surface 810, and is able to be released from the ball detent 830, leading to separation of the blade 600 and imager module 200. FIG. 8 also shows the handle 610 being connected to distal part 650 of the blade 600.

In certain embodiments, when in use, the ball plunger 205 of the longitudinal member 210 locks into the ball detent 830 on the inside surface of the handle 610 of the blade 600 to lock the blade 600 to the longitudinal member 210.

In certain embodiments, the ball plunger 205 may be flexible and may have a spring (not shown) between it and the outer surface of the longitudinal shaft 210, such that when force is exerted on the ball plunger 205 by the inner surface of the handle 610, it retracts into the longitudinal member 210. However, when the ball plunger 205 is aligned with the ball detent 830, no force is provided on the ball plunger 205 and it is forced outward by the spring. The ball plunger 205 and ball detent 830 are then locked in place and the imager module 200 is secured to the blade 600.

Figure 9:
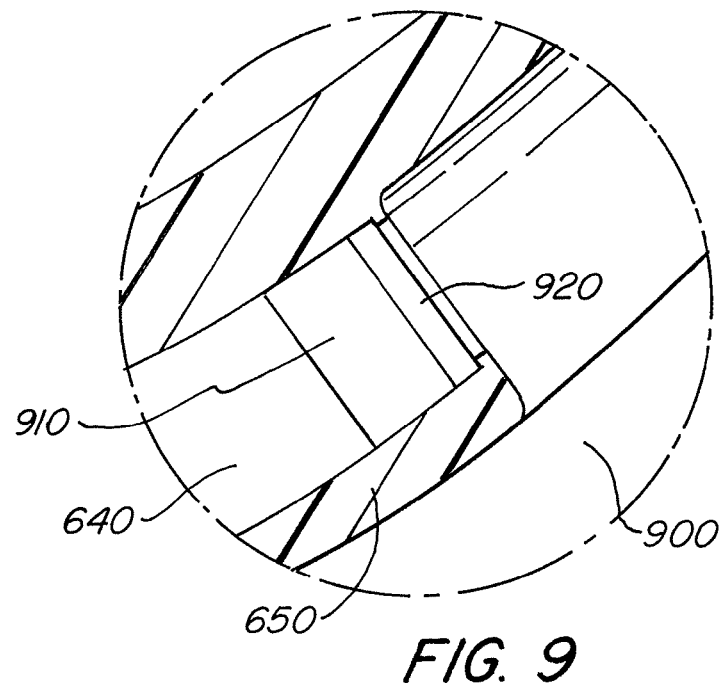
FIG. 9 is an exploded detail view along axis 9 of FIG. 7.

To release the imager module 200 from the blade 600, a user may exert pressure downwards so that the ball plunger 205 is released from the ball detent 830, thus releasing the securing mechanism between these two elements. A user may also rotate the imager module 200 within the blade 600, thus, providing a releasing mechanism between these two elements. In certain embodiments, the shape of the imager module actually prevents rotation, as it is form-fit with the blade. Thus, incorrect insertion of the imager module into the blade is prevented FIG. 9 is an exploded detail view of section 8 of FIG. 7. FIG. 9 shows channel 640 formed in the distal part 650 of the blade 600. In this section lens 910 is shown as well as lens cover 920. A lens may be provided over the end of the camera of the cable 250 in certain embodiments of the invention. The lens 910 may be a single lens, doublet lens, fish eye lens, or other known lens used for intubation systems known in the art.

Figure 10:
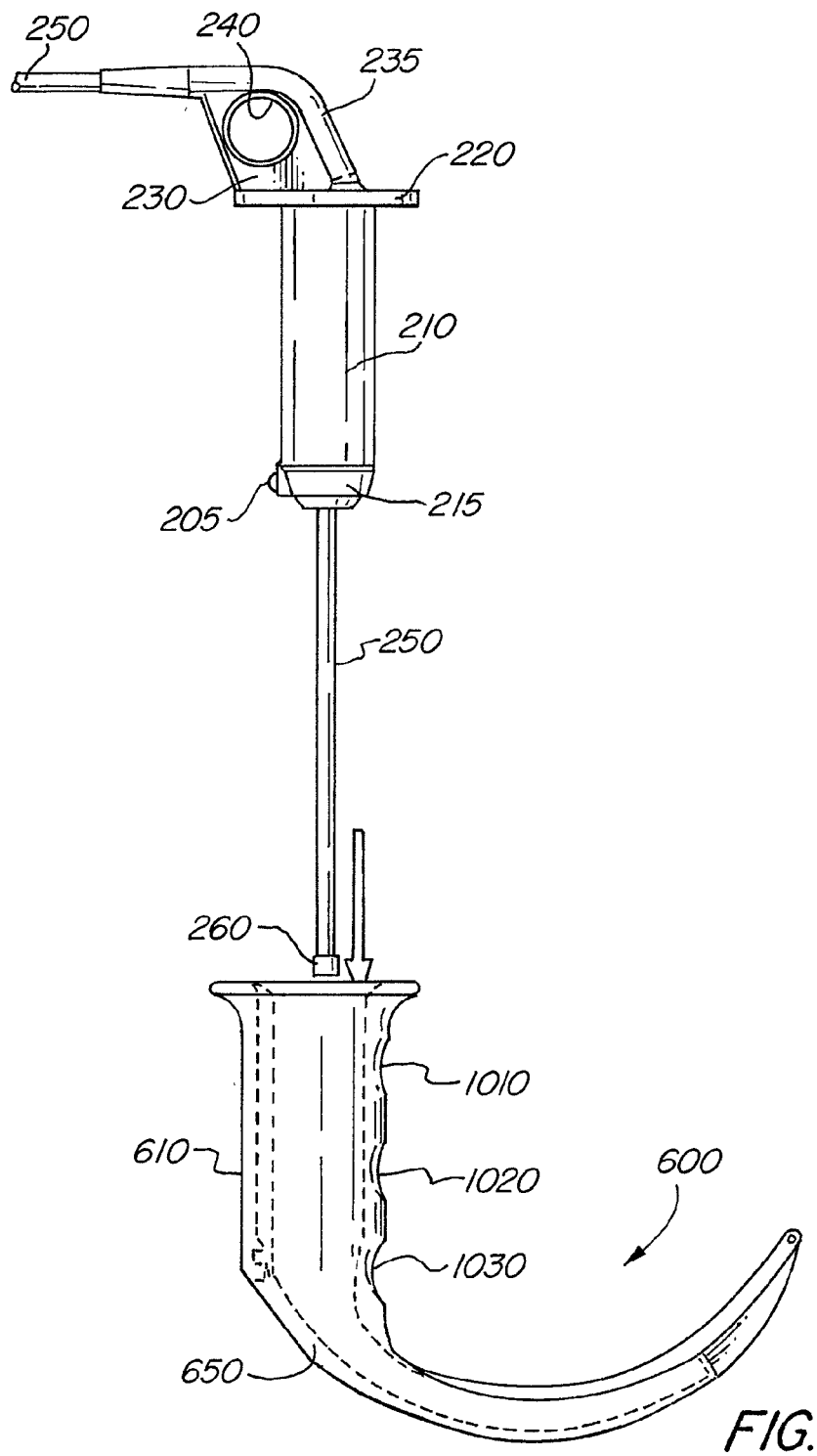
FIG. 10 is an exploded view of the imager module and blade of FIG. 1.

FIG. 10 is an exploded view of the imager module and blade of FIG. 1. Here the imager module 210 is shown being able to be inserted into the blade 600, specifically handle 610. Furthermore, ridges 1010, 1020 and 1030 are shown on the handle 610, the ridges allowing a user to easily grip the handle 610.

Figure 11:
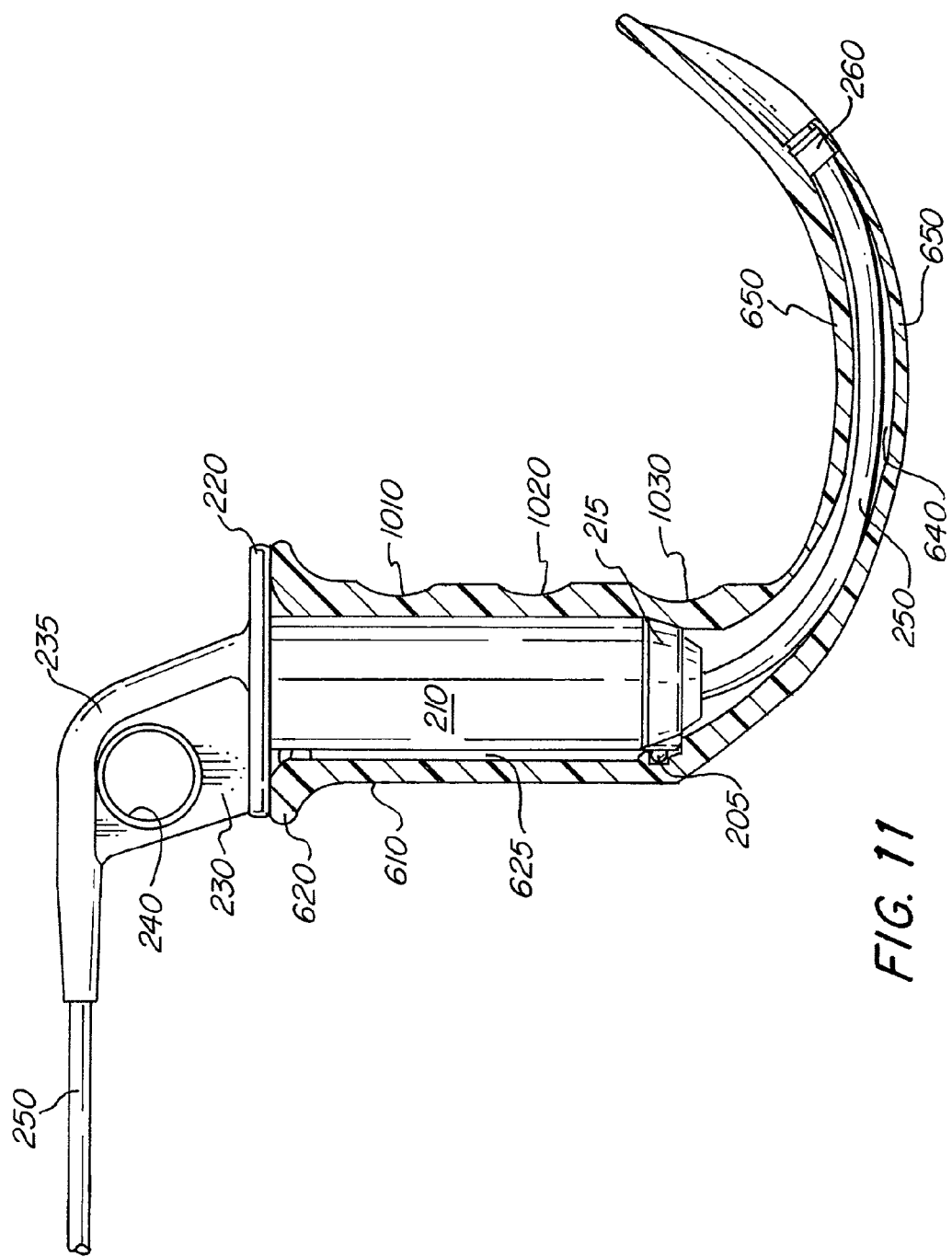
FIG. 11 is a cross section view of the imager module and blade of FIG. 1.

FIG. 11 is a cross section view of the imager module 200 inserted into the blade 600. The flange 220 of the base unit 230 is shown abutting against the proximal end 620 of the handle 610. Furthermore, the cable 250 is shown within channel 640. The cable 250 is shown as being flexible and not filing the entire channel 640.

Furthermore, FIG. 11 shows various elements of base unit 230, including loop 235, which encloses cable 250, as well as finger loop 240. The loop 235 in base unit 230 makes it difficult for the cable to be removed from the imager module, so that a user does not just pull the cable causing possible damage to the cable connection.

Furthermore, the finger loop 240 makes it easier to remove the longitudinal member 210 and prevents kinking of the cable during use. Moreover, the finger loop 240 helps lead the cable away from the instrument and from the patient so it is not in the way during intubation. This is because the cable 250 is parallel to the distal part 650 of the blade and is not in the way when a patient is being intubated.

The laryngoscopes of the invention come in different blade sizes and shapes for different patients and intubation situations. Such intubation situations include intubating children or adults, obese patients, and patients whose neck may not be moved or who are bleeding in the throat.

In certain embodiments, the blade 600 may have different shapes that are commonly used in laryngoscopes. In certain embodiments, the blade may be a Macintosh blade or a Miller blade. In certain embodiments, the blade may be a Dörges blade (D-blade). In certain embodiments, one imager module may be used with different disposable blades and may be form-fit to different disposable blades.

While the invention has been specifically described in connection with certain specific embodiments thereof, it is to be understood that this is by way of illustration and not of limitation, and that various changes and modifications in form and details may be made thereto, and the scope of the appended claims should be construed as broadly as the prior art will permit.

The description of the invention is merely exemplary in nature, and, thus, variations that do not depart from the gist of the invention are intended to be within the scope of the invention. Such variations are not to be regarded as a departure from the spirit and scope of the invention.

What is claimed is:

1. An intubation instrument comprising:
   an imager module, the imager module including
   a base unit having a proximal end and a distal end, the proximal end of the base unit having a finger loop, the base unit further including a hollow portion having a loop, the hollow portion adapted to receive electronic wiring, and
   a longitudinal member, the longitudinal member attached to the distal end of the base unit and projecting longitudinally away from the distal end of the base unit; and
   a blade, the blade having a proximal end and a distal end, the proximal end forming a handle that is hollow and that mates with an outer surface of the longitudinal member forming a male-female connection, and the distal end of the blade projecting laterally therefrom, the distal end of the blade being insertable into a human during intubation.

2. The intubation instrument of claim 1, wherein the base unit includes a flange at the distal end of the base unit, the flange on the base unit abutting against a flange in the proximal end of the blade.

3. The intubation instrument of claim 1, wherein the longitudinal member includes a ball plunger on an outside surface of the longitudinal member.

4. The intubation instrument of claim 3, wherein the blade includes a ball detent on an inside surface of the handle of the blade, the ball detent adapted to interact with the ball plunger of the longitudinal member so that the longitudinal member and blade are connected with each other during use of the intubation instrument.

5. The intubation instrument of claim 4, wherein when in use, the ball plunger of the longitudinal member locks into the ball detent on the inside surface of the handle of the blade to lock the blade to the longitudinal member.

6. The intubation instrument of claim 1, further comprising electronic wiring, the electronic wiring containing a camera at its distal end.

7. The intubation instrument of claim 6, wherein the imager module and the blade are adapted to receive the electronic wiring, the electronic wiring passing through the imager module and the blade.

8. The intubation instrument of claim 6, wherein the electronic wiring is connected to a display for displaying images received by the camera.

9. The intubation instrument of claim 8, wherein the electronic wiring is partially contained within the distal end of the blade.

10. The intubation instrument of claim 1, wherein the blade includes a guide located within the handle of the blade, the guide including a channel.

11. The intubation instrument of claim 10, wherein the channel is adapted to receive electronic wiring, the electronic wiring containing a camera at its distal end.

12. The intubation instrument of claim 11, wherein the channel in the blade is sandblasted for easier insertion and removal of the electronic wiring.

13. The intubation instrument of claim 1, wherein the longitudinal member includes electronics to control the imager module.

14. The intubation instrument of claim 1, wherein said blade is disposable.

15. The intubation instrument of claim 1, wherein said blade is made of plastic or a hard polymer material.

16. The intubation instrument of claim 1, wherein the intubation instrument is a video laryngoscope.

17. The intubation instrument of claim 1, wherein the imager module is separable from the blade, wherein the imager module is disinfected after being used and the blade is disposed of after use.

18. The intubation instrument of claim 1, wherein the electronic wiring is flexible.

19. The intubation instrument of claim 1, wherein the blade includes a lens at its distal end.

20. An intubation instrument comprising:
    an imager module, the imager module including
    a base unit having a proximal end and a distal end, the proximal end of the base unit having a finger loop, the base unit further including a hollow portion having a loop, the hollow portion adapted to receive electronic wiring, and
    a longitudinal member, the longitudinal member attached to the distal end of the base unit and projecting longitudinally away from the distal end of the base unit, the longitudinal member having a ball plunger on an outside surface of the longitudinal member; and
    a blade, the blade having a proximal end and a distal end, the proximal end forming a handle that is hollow and that mates with an outer surface of the longitudinal member forming a male-female connection such that a portion of the longitudinal member is located within the blade, and the distal end of the blade projecting laterally therefrom, the distal end of the blade being insertable into a human during intubation, the blade including a ball detent on an inside surface of the handle of the blade, the ball detent adapted to interact with the ball plunger of the longitudinal member so that the longitudinal member and the blade are connected with each other during use of the intubation instrument,
    wherein when in use, the ball plunger of the longitudinal member locks into the ball detent on the inside surface of the handle of the blade to lock the handle to the longitudinal member and handle.

21. The intubation instrument of claim 20, wherein the blade is disposable blade.

22. The intubation instrument of claim 20, wherein the intubation instrument is a laryngoscope.

* * * * *